(12) United States Patent
Walborn et al.

(10) Patent No.: US 8,016,790 B2
(45) Date of Patent: Sep. 13, 2011

(54) INFUSION STATUS INDICATOR

(75) Inventors: Jonathan Walborn, San Diego, CA (US); Roger Greenwald, San Diego, CA (US); Rena Bradham, Carlsbad, CA (US)

(73) Assignee: CareFusion 303, Inc., San Diego, CA (US)

( * ) Notice: Subject to any disclaimer, the term of this patent is extended or adjusted under 35 U.S.C. 154(b) by 339 days.

(21) Appl. No.: 11/738,296

(22) Filed: Apr. 20, 2007

(65) Prior Publication Data

US 2008/0262441 A1    Oct. 23, 2008

(51) Int. Cl.
*A61M 1/00* (2006.01)

(52) U.S. Cl. .......................... 604/153; 604/247; 417/163

(58) Field of Classification Search .................. 604/132, 604/140, 153, 247; 417/163
See application file for complete search history.

(56) References Cited

U.S. PATENT DOCUMENTS

| | | | |
|---|---|---|---|
| 3,675,722 A * | 7/1972 | Balmes, Sr. ..................... 169/30 |
| 3,993,069 A | 11/1976 | Buckles | |
| 4,867,740 A * | 9/1989 | East .................................. 604/9 |
| 5,013,303 A | 5/1991 | Tamari | |
| 5,813,842 A | 9/1998 | Tamari | |
| 5,840,071 A | 11/1998 | Kriesel | |
| 5,954,696 A | 9/1999 | Ryan | |
| 6,165,154 A | 12/2000 | Gray | |
| 6,312,409 B1 * | 11/2001 | Gross ............................ 604/131 |
| 6,338,728 B1 | 1/2002 | Valerio | |
| 6,709,417 B1 * | 3/2004 | Houle et al. .................. 604/153 |
| 2002/0177809 A1* | 11/2002 | Kriesel et al. ................ 604/132 |
| 2003/0163112 A1 | 8/2003 | Makkink | |

* cited by examiner

*Primary Examiner* — Theodore J. Stigell
*Assistant Examiner* — Brandy C Scott
(74) *Attorney, Agent, or Firm* — McDermott Will & Emery LLP

(57) ABSTRACT

An infusion status indicator disposed in the medical infusion line includes a housing with an opening through which the status of the infusion may be determined. A flexible membrane is located at the opening to indicate the status of fluid in the cavity. A recessed flexible membrane indicates insufficient flow of medical fluid into the cavity from the fluid supply, a level flexible membrane indicates correct flow of fluid through the indicator, and a concave flexible membrane indicates an insufficient flow of medical fluid out of the cavity, possibly indicating an occlusion of the fluid line downstream of the indicator. Check valves may be included upstream and downstream of the cavity so that a bolus of fluid may be forced out of the cavity to the patient by pressing the flexible membrane into the cavity.

19 Claims, 3 Drawing Sheets

INFUSION STATUS INDICATOR

BACKGROUND OF THE INVENTION

The invention is related generally to fluid delivery devices, and more particularly, to a status indicator for indicating the status of the flow of medical fluid through an administration device.

In the past, prolonged infusion of fluids has often been accomplished using gravity flow methods, which typically involve the use of intravenous administration sets and a bottle or bag of medical fluid suspended above the patient. Such methods are cumbersome, imprecise, and require bed confinement of the patient. Periodic monitoring of the apparatus by the nurse or doctor is required to detect malfunctions of the infusion apparatus.

The apparatus of the present invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and other medicinal agents. Similarly, the devices can be used for IV chemotherapy and can accurately deliver fluids to the patient in precisely the correct quantities and rates over time.

The present invention is directed, generally, to an ambulatory drug infusion pump for administering antibiotics, antiviral, and other IV medications for critically ill patients and for home care or out-patient applications.

In many situations, a patient may require multiple daily therapies, intermittent infusion, or a slow and continuous introduction of medicament liquid into the patient's system. Moreover, certain therapies require medicament liquid or pharmaceutical solutions to be infused over a particular period of time which may range anywhere from about 30 minutes to about several hours, for a therapeutic dose. It is therefore very important that these medicament liquid or pharmaceutical solution doses be administered completely and with a highly accurate introduction rate (flow rate). Currently, a variety of devices exist that are able to deliver medicament liquids and pharmaceutical solutions intravenously to a patient. In the past few years, certain of these devices have offered some degree or portability, but the most widely utilized of these devices typically require a patient to be confined to a bed, thus limiting the options available for patients who are able to be ambulatory.

So called ambulatory infusion pumps are gaining currency in medical technology, given the trend towards shorter hospital stays and increasing reliance on out-patient and home care treatment. Such ambulatory devices typically function on an infusion pump delivery principle which pumps a medicament liquid or other IV solution into the patient. The pressure developed by the infusion pump is designed to overcome the resistance of the patient's internal pressure and include regulators or restrictors in the IV tubing set to attempt to control the rate of flow of the IV solution into the patient. For example, it is common to pressurize a container filled with a medicament liquid or IV solution by transmitting a hydrostatic or gas pressure developed in an external or internal gas-filled bladder to the IV solution container. By maintaining a constant pressure in the bladder, it was hoped that the bladder would exert (transmit) a constant pressure to the IV solution container, thereby developing a constant flow rate of medicament liquid at the point of infusion.

In the more common elastomeric-type infusion pump devices, the elastomeric pumps use the pressure of an expanding elastomeric element to push an IV solution through a rate controlling orifice or a constrictive clamp. However, the flow rate of these systems are prone to several external factors which are beyond the control of the device and are not outwardly obvious to an uninitiated patient administering the infusion.

The reality with prior art systems is that ambulatory patients are not readily able to determine the status of fluid flow in their infusion system. Thus, patients tend to verify the status of their infusions by disconnecting the pump from the catheter (i.e. break the line) to see if drops form. This practice of breaking the line exposes the infusion line to outside contaminants, creating an infection risk and potentially putting the patient in contact with hazardous chemicals.

Hence, those skilled in the art have recognized a need for a flow indicator device that is easily monitored by a home user to determine if fluid is flowing in the administration line. Further, those skilled in the art have recognized the need for an indicator device that can be used to provide a bolus of medication to a patient. The present invention fulfills these needs and others.

SUMMARY OF THE INVENTION

Briefly and in general terms, the present invention is directed to an indicator device for indicating the status of medical fluid flow through an infusion line, the indicator device comprising a housing surrounding a cavity through which the fluid may flow, the housing having a fluid inlet adapted to be coupled to a portion of the infusion line from which fluid would flow into the housing, a fluid outlet adapted to be coupled to a portion of the infusion line into which fluid would flow out of the housing, and an indicator opening that provides fluid communication with fluid residing in the cavity; and a flexible membrane disposed at the indicator opening in contact with fluid in the cavity, the membrane having a moveable membrane portion configured to move in relation to the opening in response to pressure of fluid in the cavity such that the movable membrane portion has a first position when fluid is flowing through the cavity and a second position when fluid is not flowing through the cavity, the first and second positions being distinguishable either by visual and/or tactile means.

In more detailed aspects, the indicator device further comprises an inlet flow restrictor disposed in the portion of the fluid line from which the fluid flows into the cavity, the inlet flow restrictor providing a first flow resistance to flow of medical fluid into the cavity. The indicator device further comprises an outlet flow restrictor disposed in the portion of the fluid line into which the fluid flows out of the cavity, the outlet flow restrictor providing a second flow resistance to flow of medical fluid out of the cavity. In a further aspect, in one case the second flow resistance is greater than the first flow resistance, and in another aspect the first flow resistance is greater than the second flow resistance. In much further detail, the flow restrictors are formed as part of the housing of the indicator.

In other aspects in accordance with the invention, the moveable membrane portion is configured to recess into the cavity when the flow rate of fluid through the cavity is at a first threshold, the moveable membrane portion is configured to extend approximately level with the opening of the housing when the flow rate of fluid through the cavity is at a second threshold, and the moveable membrane portion is configured to protrude outwardly from the opening of the housing when the flow rate of fluid through the cavity is at a third threshold.

The second threshold is greater than the first threshold and the third threshold is greater than both the first threshold and the second threshold.

In another aspect, the indicator device further comprises a position indicator disposed on the moveable membrane portion, the position indicator configured to provide a visual indication of the position of the moveable portion in respect to the opening to more clearly visually indicate the status of fluid flow through the fluid line.

In yet a further aspect, the movable membrane portion is configured to have a first position, a second position, and a third position, such that the moveable membrane portion is located in the first position when fluid in the cavity has a first predefined fluid pressure that represents that the flow rate of fluid into the cavity is insufficient, the movable membrane portion is located in the second position when fluid in the cavity has a second predefined fluid pressure greater than the first predefined fluid pressure that represents a sufficient flow rate into and out of the cavity, and the movable membrane portion is located in the third position when fluid in the cavity has a third predefined fluid pressure greater than the second predefined fluid pressure that represents that the rate of flow of fluid out of the cavity is insufficient. In more detailed aspects, the first predefined pressure is about 0 kPa (0 psi), the second predefined pressure is about 24 kPa (3.5 psi), and the third predefined pressure is about greater than 48 kPa (7 psi).

In yet other aspects, the indicator device further comprises a check valve located upstream of the cavity, the check valve configured to permit the flow of fluid into the cavity and prevent the flow of fluid out of the cavity. Further in accordance with another aspect, the indicator device further comprises a check valve located downstream of the cavity, the check valve configured to permit the flow of fluid out of the cavity and prevent the flow of fluid into the cavity. And yet further, the indicator device comprises a bolus device located at the indicator opening in contact with the flexible membrane, and configured such that pressing the bolus device into the cavity produces a bolus of fluid from the cavity out the fluid outlet.

These and other aspects, features, and advantages of the present invention will become apparent from the following detailed description of the preferred embodiments which, taken in conjunction with the accompanying drawings, illustrate by way of example the principles of the invention.

DETAILED DESCRIPTION OF THE INVENTION

The invention comprises a method and apparatus for indicating the status of an infusion to a patient. In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In general, one or more embodiments of the invention comprise a fluid flow indicator device coupled to an infusion line. The fluid flow indicator comprises a fluid pressure chamber, a flexible (pressure sensitive) elastomeric membrane attached to the chamber. Additionally, a visually distinguishable or tactile device (e.g. a piece of plastic material to provide indication of the position of the membrane by visual inspection or by feel) may be attached in the vicinity of the center of the membrane to further provide easy flow status cues to the patient or care giver. Fluid flow restrictors may also be coupled on the upstream and downstream ends of the indicator device to control pressure in the chamber and to control the fluid flow rate through the chamber. Preferably, the upstream restrictor provides less restriction than the downstream restrictor.

The membrane in one or more embodiments of the indicator device is configured to have a concave shape protruding into the pressure chamber to indicate that the infusion has not been started or has been stopped or ended (i.e. no pressure from the pressure source). As the infusion progresses, the pressure in the chamber increases (to the source pressure minus the upstream pressure drop) causing the membrane to deform into a flat position. When the downstream line is occluded, the pressure in the chamber increases to the source pressure causing the membrane to protrude from the pressure chamber.

Figure 1:
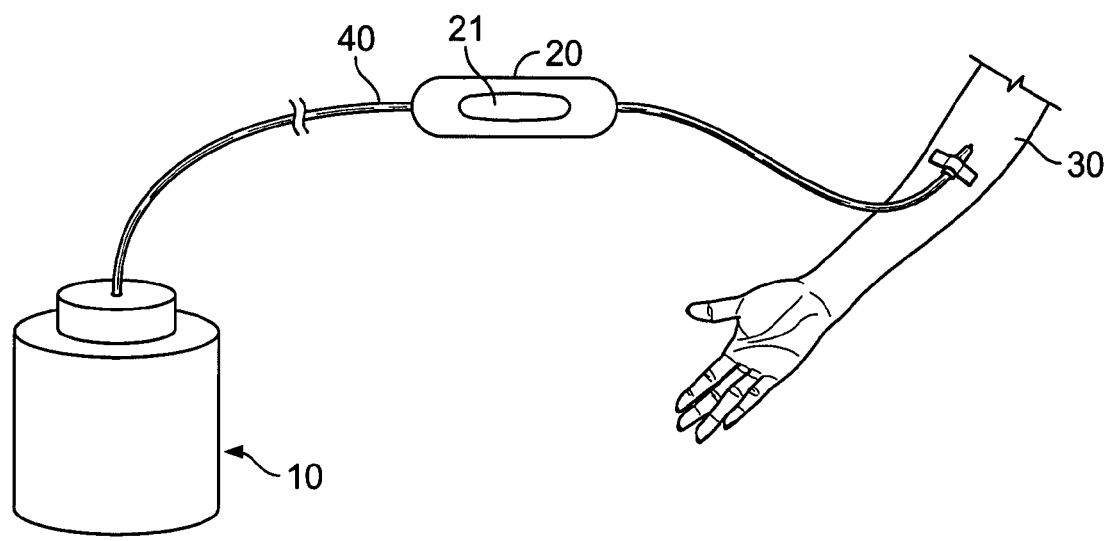
FIG. 1 depicts an elastomeric powered fluid pump in which is contained medical fluid and a medical fluid administration set comprising a conduit or fluid line that conducts the medical fluid from the supply to a patient, and a fluid flow indicator device in accordance with aspects of the invention in a fluid administration set.

Embodiments of the present inventions would now be described with reference to FIGS. 1-5. Referring now to the drawings in more detail in which like reference numerals refer to like or corresponding devices among the views, there is shown in FIG. 1 a fluid flow indicator device 20 in accordance with aspects of the invention located within a fluid administration set used to deliver medical fluid to an ambulatory or home patient 30. In particular, a fluid container or supply 10 taking one of many forms, such as an elastomeric membrane-powered pump, bag, bottle, or other pressurized container, is connected with the patient through a conduit or tubing 40. The fluid conduit 40 conducts the fluid downstream from the fluid supply to the indicator device 20 and then further downstream to the patient. As used herein only for convenience and not for a purpose of limitation, "upstream" shall refer to the direction towards the supply 10, and "downstream" shall refer to the direction towards the patient 30.

In accordance with aspects of the invention, a patient 30 or user of the administration system of FIG. 1 can determine the status of the flow of medical fluid through the line 40 by observing the indicator device 20. In particular, the status indicator device in FIG. 1 includes a window or opening 21 in which a flow level membrane may be attached in direct contact with fluid in the housing. The membrane is preferably flexible and its position in relation to the opening is configured to indicate to the user whether sufficient flow of medical fluid to the patient is occurring or if there is a problem.

Figure 2:
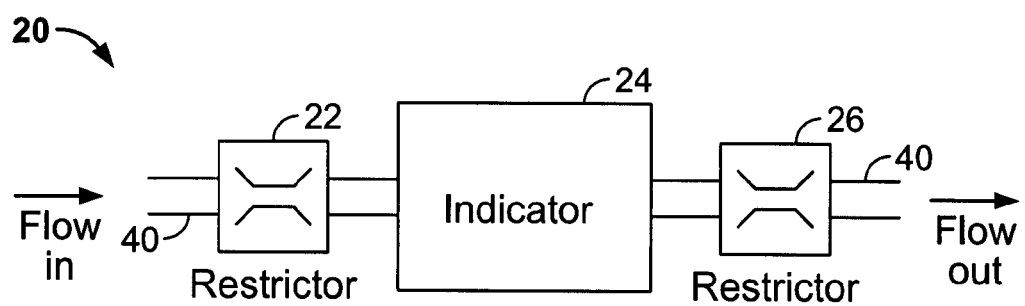
FIG. 2 is a functional illustration of the fluid flow status indicator device 20 of FIG. 1.

In one or more embodiments, the status indicator device is configured as illustrated in FIG. 2. As illustrated, status indicator device 20 comprises Upstream Restrictor component 22, Indicator component 24, and Downstream Restrictor component 26. Infusion fluid enters through Upstream Restrictor component 22 and flows through indicator component 24 and Restrictor component 26. Restrictor component 26, which is preferably more restrictive than Restrictor component 22, causes buildup of pressure in indicator component 24 thus causing indicator component 24 to react to the pressure, as illustrated in FIGS. 3A-3C.

Figure 3A:
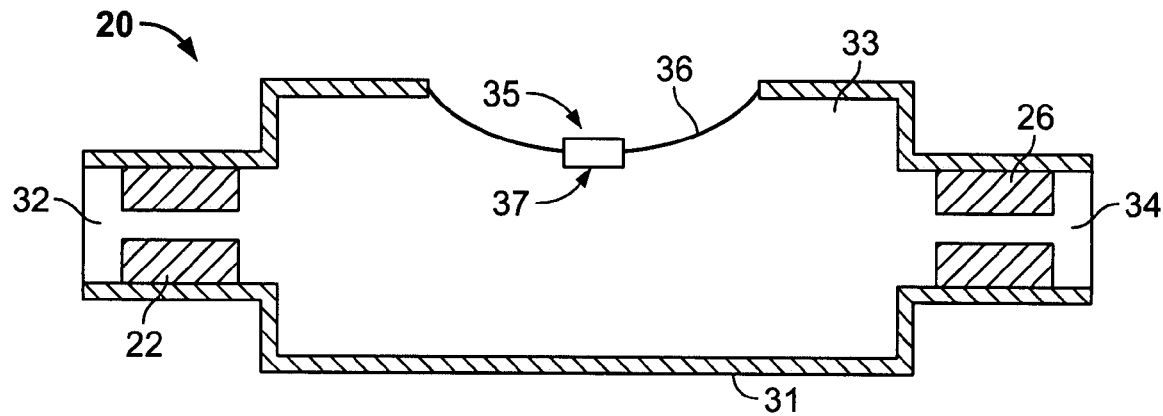
FIG. 3A is a cross-sectional view of the fluid flow status indicator device of FIG. 1 showing a housing, an inlet, a first fluid flow restrictor at the inlet, an outlet, a second fluid flow restrictor at the outlet, a cavity between the inlet and outlet, and a membrane in the resting position showing insufficient or no fluid pressure through the infusion line.
Figure 3B:
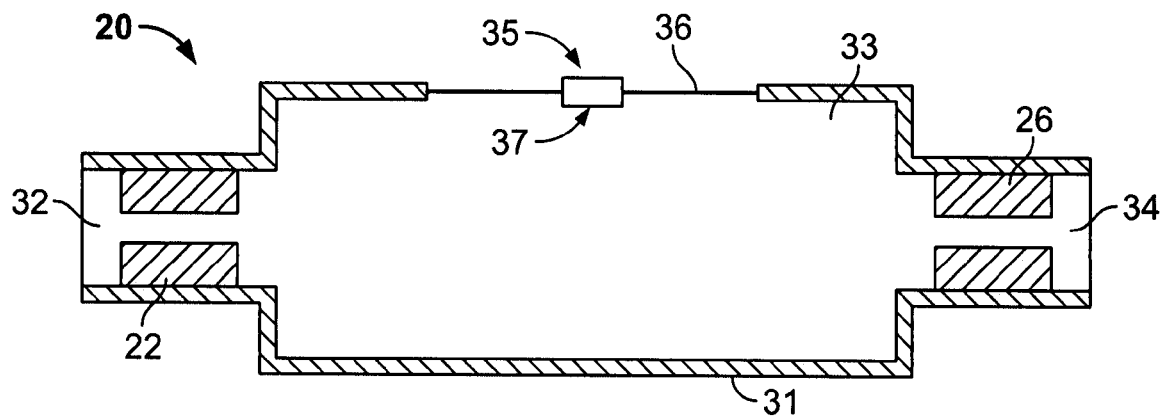
FIG. 3B is a cross-sectional view of the fluid flow status indicator device of FIG. 1 showing a housing, an inlet, a first fluid flow restrictor at the inlet, an outlet, a second fluid flow restrictor at the outlet, a cavity between the inlet and outlet, and a membrane in the normal position showing sufficient fluid pressure through the infusion line.
Figure 3C:
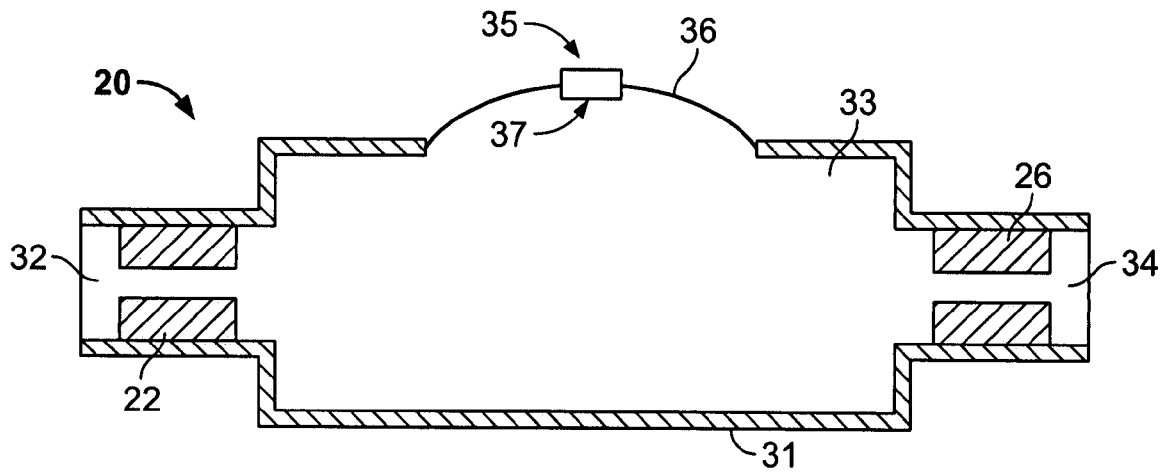
FIG. 3C is a cross-sectional view of the fluid flow status indicator device of FIG. 1 showing a housing, an inlet, a first fluid flow restrictor at the inlet, an outlet, a second fluid flow restrictor at the outlet, a cavity between the inlet and outlet, and a membrane in the occluded position showing possible blockage downstream of the cavity.

Referring now to FIGS. 3A-3C, a cross-sectional view of one embodiment of status indicator 20 in accordance with aspects of the invention is illustrated. The status indicator includes a housing 31, an inlet port 32, a cavity 33, and an output port 34. An opening 35 permits the patient, nurse, or other clinician to determine the status of fluid flow through the status indictor device. In the opening, a flexible membrane 36 may be disposed to move in the indicator device in accordance with fluid pressure in the housing. In addition, a piece of material acting as a position indicator 37 (e.g. a plastic indicator) may be coupled to the membrane to provide easy visual feedback of the flow status. Position indicator 37 may be configured to provide visual or tactile cues of the flow status, for instance.

The flexible membrane 36 is mounted at the opening 35 and moves in relation thereto to indicate the amount of pressure of the medical fluid disposed within the cavity. As shown in FIG. 3A, the membrane is recessed within the cavity away from the opening thereby indicating insufficient pressure within the cavity. If the membrane were to be level with the opening, as shown in FIG. 3B, the pressure of the medical fluid within the cavity would be sufficient to accomplish the patient's infusion. If the membrane protrudes outwardly from the opening of the housing, as illustrated in FIG. 3C, the pressure within the cavity is too high thus indicating that the downstream portion of the administration line may be occluded. The flexible membrane may be configured with a protective shell to prevent tampering.

In another embodiment of the present invention, the indictor could be used as a bolus device for pain management. In this case the membrane would have two states, concave (protruding into the pressure chamber) which would indicate that no bolus is available and convex (protruding out of the pressure chamber which would indicate that a bolus could be delivered. In this configuration, the upstream restriction would be more restrictive than the downstream restriction to ease delivery of the bolus volume while allowing the bolus device to refill slowly. This prevents the patient from administering several immediate bolus doses, as well as permitting a constant flow of fluid while the bolus volume is refilled. In addition, a check valve may be required on the pressure chamber input to prevent backflow during bolus delivery.

Figure 4:
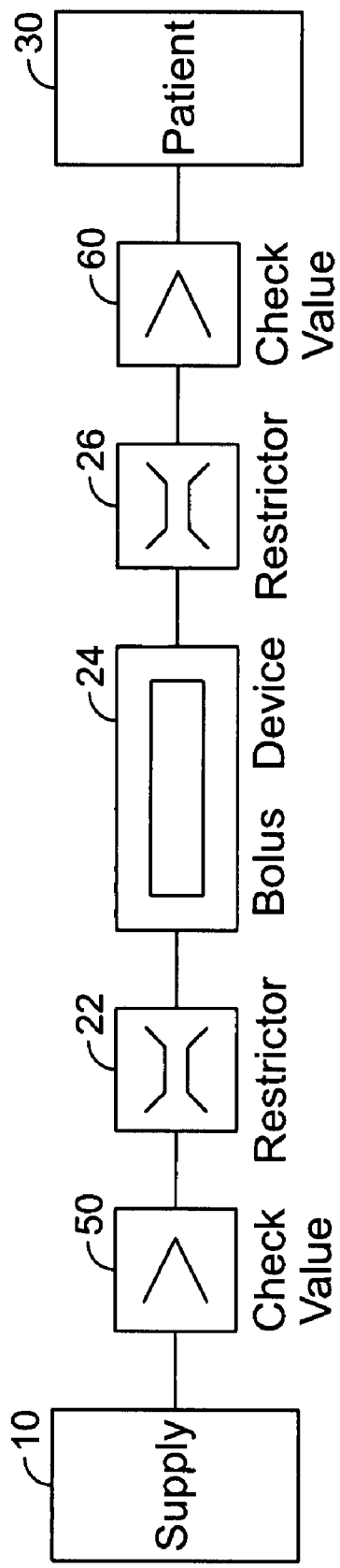
FIG. 4 is a schematic diagram of a flow indicator and bolus administration system in accordance with aspects of the invention showing check valves, flow restrictors, and the flow indicator of FIG. 1.

FIG. 4 is a functional illustration of an embodiment of the present invention when used as a bolus device. As illustrated, an upstream check valve 50 is added between the Supply 10 and Restrictor 22 to prevent backflow of fluid during bolus delivery. In addition, a downstream check valve 60 may be required between Restrictor 26 and the patient to prevent back flow of the bolus dose into the chamber.

Figure 5:
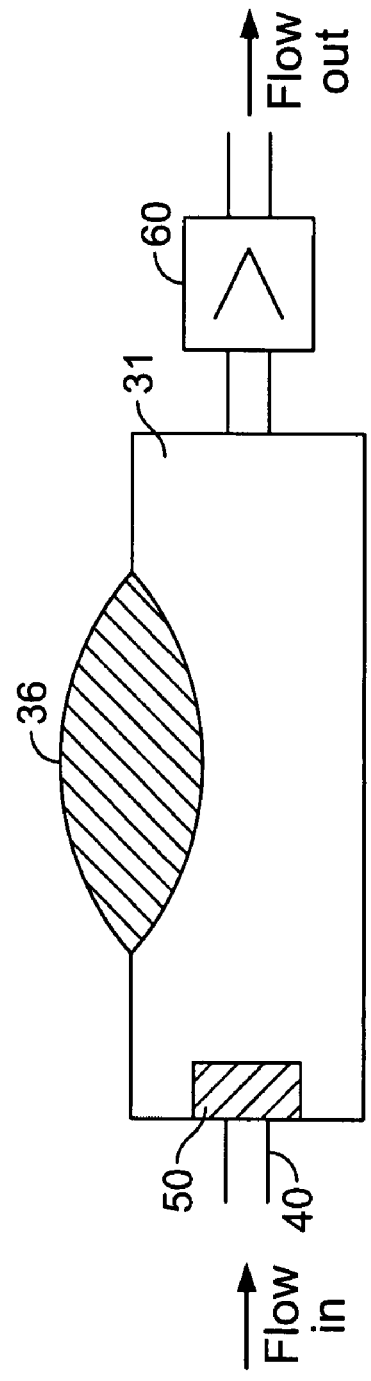
FIG. 5 is a perspective view of an embodiment of the present invention when used as a bolus device.

FIG. 5 is a perspective view of an embodiment of the present invention when used as a bolus device. As configured, check valve 50 is coupled into housing 31 and the flexible membrane protrudes in a convex form out of the pressure chamber when a bolus is ready to be delivered to the patient. To deliver the bolus to the patient, the user depresses the membrane thereby forcing the medical fluid to exit the chamber through the Flow Out opening.

In summary, the embodiments presented and discussed above provide a device that gives an indication of whether a given infusion with an elastomeric infusion pump has started, is running, or is occluded. The status indicator device comprises a fluid pressure cavity and a flexible elastomeric membrane attached to the cavity. Additionally, a position indicator (e.g. a plastic material) may be mounted on the membrane, preferably in the vicinity of the center, to further provide feedback (e.g. visual or tactile) of the position of the membrane. Fluid flow restrictors are placed on the upstream and downstream ends of the status indicator device in one embodiment to control pressure in the cavity and to control the fluid flow rate. The device is provided with the membrane in a concave shape, receding into the pressure cavity. This position indicates that the infusion has not been started or has been stopped or ended (no pressure from the pressure source). As the infusion progresses, the pressure in the chamber increases causing the membrane to deform into a flat position. When the downstream line is occluded, the pressure in the chamber increases to the source pressure causing the membrane to protrude outwardly from the pressure cavity. The plastic indicator would improve differentiation of these various conditions. In an alternate embodiment, the indicator could be used as a bolus device for the purposes of pain management. In this embodiment, the indicator has two states the first of which is concave, that indicates that no bolus is available and the second of which is convex which indicates that a bolus could be delivered.

Although the present invention has been described in terms of certain embodiments, other embodiments that are apparent to those of ordinary skill in the art are also within the scope of the invention. It will be understood that the above described arrangements of apparatus and the method therefrom are merely illustrative of applications of the principles of this invention and many other embodiments and modifications may be made without departing from the spirit and scope of the invention as defined in the claims.

What is claimed is:

1. An indicator device for indicating the status of a flow of a fluid through an infusion line, the indicator device comprising:
   a housing surrounding a cavity through which the fluid may flow, the housing having a fluid inlet adapted to be coupled to a portion of the infusion line from which the fluid would flow into the housing, a fluid outlet adapted to be coupled to a portion of the infusion line into which the fluid would flow out of the housing, and an indicator opening;
   a flexible membrane disposed at the indicator opening in contact with the fluid in the cavity, the flexible membrane having a moveable membrane portion configured to move in relation to the indicator opening in response to pressure of the fluid in the cavity to provide distinguishable cues of a status of the flow of the fluid through the infusion line; and a position indicator disposed in the vicinity of the center of the moveable membrane portion and on an exterior surface of the indicator device, the position indicator configured to provide, by reciprocating linear movement in response to the status of the flow of the fluid through the fluid line, a tactile indication of a position of the moveable membrane portion with respect to the indicator opening.

2. The indicator device of claim 1, further comprising:
an inlet flow restrictor disposed in the portion of the fluid line from which the fluid flows into the cavity, the inlet flow restrictor providing a first flow resistance to flow of the fluid into the cavity.

3. The indicator device of claim 2, further comprising:
an outlet flow restrictor disposed in the portion of the fluid line into which the fluid flows out of the cavity, the outlet flow restrictor providing a second flow resistance to flow of the fluid out of the cavity.

4. The indicator device of claim 3, wherein the second flow resistance is greater than the first flow resistance.

5. The indicator device of claim 2, wherein the inlet flow restrictor is formed as part of the housing.

6. The indicator device of claim 3, wherein the outlet flow restrictor is formed as part of the housing.

7. The indicator device of claim 1, further comprising:
an outlet flow restrictor disposed in the portion of the fluid line into which the fluid flows out of the cavity, the outlet flow restrictor providing a second flow resistance to flow of the fluid out of the cavity.

8. The indicator device of claim 1, wherein the moveable membrane portion is configured to recess into the cavity when the flow rate of the fluid through the cavity is at a first threshold.

9. The indicator device of claim 8, wherein the moveable membrane portion is configured to extend approximately level with the indicator opening when the flow rate of the fluid through the cavity is at a second threshold.

10. The indicator device of claim 9, wherein the moveable membrane portion is configured to protrude outwardly from the indicator opening when the flow rate of the fluid through the cavity is at a third threshold.

11. The indicator device of claim 10, wherein the second threshold is greater than the first threshold and the third threshold is greater than both the first threshold and the second threshold.

12. The indicator device of claim 1, wherein the moveable membrane portion is configured to extend approximately level with the indicator opening when the flow rate of the fluid through the cavity is at a second threshold.

13. The indicator device of claim 1, wherein the moveable membrane portion is configured to protrude outwardly from the indicator opening when the flow rate of the fluid through the cavity is at a third threshold.

14. The indicator device of claim 1, further comprising:
a position indicator disposed on the moveable membrane portion, the position indicator configured to provide a visual indication of the position of the moveable membrane portion in respect to the indicator opening to more clearly visually indicate the status of fluid flow through the fluid line.

15. The indicator device of claim 1, wherein the movable membrane portion is configured to have a first position, a second position, and a third position, such that the moveable membrane portion is located in the first position when the fluid in the cavity has a first predefined fluid pressure that represents that the flow rate of the fluid into the cavity is insufficient, the movable membrane portion is located in the second position when the fluid in the cavity has a second predefined fluid pressure greater than the first predefined fluid pressure that represents a sufficient flow rate into and out of the cavity, and the movable membrane portion is located in the third position when the fluid in the cavity has a third predefined fluid pressure greater than the second predefined fluid pressure that represents that the rate of flow of the fluid out of the cavity is insufficient.

16. An indicator device for indicating the status of delivery of a bolus of a fluid through an infusion line to a patient, the indicator device comprising:
a housing surrounding a cavity through which the fluid may flow, the housing having a fluid inlet adapted to be coupled to a portion of the infusion line from which the fluid would flow into the housing, a fluid outlet adapted to be coupled to a portion of the infusion line into which the fluid would flow out of the housing, and an indicator opening; and
a flexible membrane disposed at the indicator opening in contact with the fluid in the cavity, the flexible membrane having a moveable membrane portion configured to move in relation to the indicator opening in response to pressure of the fluid in the cavity such that the moveable membrane portion has a first position indicating a bolus is ready for delivery and a second position when a bolus is not available for delivery; and
a position indicator disposed in the vicinity of the center of the moveable membrane portion and on an exterior surface of the indicator device, the position indicator configured to provide, by reciprocating linear movement in response to the status of the flow of the fluid through the fluid line, a tactile indication of a position of the moveable membrane portion with respect to the indicator opening.

17. The indicator device of claim 16, further comprising:
a check valve located upstream of the cavity, the check valve configured to permit the fluid to flow into the cavity and prevent the fluid to flow out of the cavity.

18. The indicator device of claim 16, further comprising:
a check valve located downstream of the cavity, the check valve configured to permit the fluid to flow out of the cavity and prevent the fluid to flow back into the cavity.

19. The indicator device of claim 16, wherein said flexible membrane is configured such that when the membrane is in the first position, pressing the membrane into the cavity causes a bolus of the fluid to flow from the cavity out the fluid outlet.

* * * * *